United States Patent [19]
Umemoto et al.

[11] Patent Number: 5,569,778
[45] Date of Patent: Oct. 29, 1996

[54] PROCESS FOR PREPARING FLUORINE-CONTAINING DICARBONYL COMPOUND

[75] Inventors: Teruo Umemoto; Ginjiro Tomizawa, both of Tsukuba, Japan

[73] Assignee: Daikin Industries Ltd., Osaka, Japan

[21] Appl. No.: 428,133

[22] PCT Filed: Nov. 1, 1993

[86] PCT No.: PCT/JP93/01584

§ 371 Date: Apr. 28, 1995

§ 102(e) Date: Apr. 28, 1995

[87] PCT Pub. No.: WO94/10120

PCT Pub. Date: May 11, 1994

[30] Foreign Application Priority Data

Oct. 30, 1992 [JP] Japan ................................ 4-315800

[51] Int. Cl.$^6$ ................................ C07C 67/287
[52] U.S. Cl. ................ 560/121; 560/125; 560/51; 560/174; 560/178; 568/316; 568/348; 568/393
[58] Field of Search ................ 560/121, 126, 560/174, 125, 51, 178; 568/316, 348, 393

[56] References Cited

FOREIGN PATENT DOCUMENTS

| 0468766 | 1/1992 | European Pat. Off. ............... 560/125 |
| 62-207228 | 9/1987 | Japan ................................ 560/125 |

OTHER PUBLICATIONS

Lerman, et al., J. Org. Chem. 1983, 48, (1983), 724–727.
Bumgardner, et al., J. Fluorine Chem., 56, (1992), 141–146.
Kagaruki, et al., Bull. Chem. Soc. Jpn., 54, (1981), 3221–3222.
Machleidt, Justus Liebigs Ann. Chim., (1964), 676,66–75.
Takeuchi, et al., J. Org. Chem., 57, (1992), 2196–2199.
Banks, et al., J. Fluorine Chem., 52, (1991), 389–401.
Umemoto, et al., J. Am. Chem. Soc., 112, (1990), 8563–8575.
Differding, et al., Tetrahedron Lett., 29, (1988), 6087–6090.
Differding, et al., Helv. Chim. Acta, 72, (1989), 1248–1252.
Yemul, et al., Tetrahedron Lett., 21, (1980), 277–280.
Zajc, et al., J. Chem. Soc., Chem. Commun., (1980), 759–760.
Xu, et al., J. Chem. Soc., Chem. Commun., (1991), 179–181.
Purrington, et al., J. Org. Chem., 52, (1987), 4307–4310.
Buchman, J. Am. Chem. Soc., 58, (1936), 1803–1805.
Fitjer, Synthesis, (1977), 189–191.
Ishikawa, et al., Chem. Lett., 1107–1110, (1980).
Kurykin, Chem. Abstracts 95:6431z (1981).

*Primary Examiner*—James H. Reamer
*Attorney, Agent, or Firm*—Birch, Stewart, Kolasch & Birch, LLP

[57] ABSTRACT

A process for preparing a fluorine-containing dicarbonyl compound of the formula: $R^1COCFR^2COR^3$ in which $R^1$ is a hydrogen atom, or a substituted or unsubstituted alkyl or aryl group; $R^2$ is a hydrogen atom, a halogen atom, or a substituted or unsubstituted alkyl or aryl group; and $R^3$ is a hydrogen atom, or a substituted or unsubstituted alkyl, aryl, alkoxy or aryloxy group, provided that at least two of $R^1$, $R^2$ and $R^3$ may together form a part of a cyclic structure with or without a hetero atom, by reacting a dicarbonyl compound of the formula: $R^1COCHR^2COR^3$ in which $R^1$, $R^2$ and $R^3$ are the same as defined above with fluorine ($F_2$) in at least one solvent selected from the group consisting of halogenated hydrocarbons having 1 to 5 carbon atoms and nitrile compounds, or in a solvent in the presence of a salt, or an acid having pKa of 6 or less.

By the above process, the fluorine-containing dicarbonyl compound is industrially prepared in a high yield.

13 Claims, No Drawings

PROCESS FOR PREPARING FLUORINE-CONTAINING DICARBONYL COMPOUND

FIELD OF THE INVENTION

This application is a 371 of PCT/JP93/01584, Nov. 1, 1993.

The present invention relates to a process for preparing a fluorine-containing dicarbonyl compound. In particular, the present invention relates to a process for preparing a fluorine-containing dicarbonyl compound from a readily available dicarbonyl compound as a raw material using a cheap fluorine gas in a single step.

PRIOR ART

A fluorine-containing dicarbonyl compound of the formula:

$$R^1COCFR^2COR^3 \tag{II}$$

wherein $R^1$ is a hydrogen atom, or a substituted or unsubstituted alkyl or aryl group; $R^2$ is a hydrogen atom, a halogen atom, or a substituted or unsubstituted alkyl or aryl group; and $R^3$ is a hydrogen atom, or a substituted or unsubstituted alkyl, aryl, alkoxy or aryloxy group, provided that at least two of $R^1$, $R^2$ and $R^3$ may together form a part of a cyclic structure with or without a hetero atom is a useful intermediate in the synthesis of agrochemicals, etc. (see EP-A-0 468 766, J. Org. Chem., 48, 724–727 (1983), J. Fluorine Chem., 56, 141 (1992), and Bull. Chem. Soc. Jpn., 54, 3221 (1981)).

As preparation processes of the fluorine-containing dicarbonyl compound of the formula (11), that is, a fluorine-containing β-diketone or β-ketoester, the following processes (1) through (5) are known:

(1) The β-diketone or β-ketoester is converted to its metal salt and then reacted with $FClO_3$ (Justus Liebigs Ann. Chim., 677, 9 (1964) and J. Org. Chem., 57, 2196 (1992)); with $CH_3COOF$ (J. Org. Chem., .48, 724 (1983)); with N-fluoroperfluoropiperidine (J. Fluorine Chem., 52, 389 (1991)); with a N-fluoropyridinium salt (J. Am. Chem. Soc., 112, 8563 (1990) and JP-A-62-207228); with N-fluorosultam (Tetrahedron Lett., 29, 6087 (1988)and Helv. Chim. Acta., 72, 1248 (1989)).

(2) The p-diketone or β-ketoester is reacted with a xenon compound ($C_{19}XeF_6$) (Tetrahedron Lett., 21,277 (1980)); with $CH_3COOF$ (J. Org. Chem., 48, 724 (1983)); with xenon difluoride in the presence of an acid catalyst (J. Chem. Soc., Chem. Commun., 1980, 759); with a N-fluoropyridinium salt in the presence or absence of an acid catalyst (J. Am. Chem. Soc., 112, 8563 (1990) and JP-A-62-207228); with N-fluorobis(trifluoromethanesulfonyl)amide (J. Chem. Soc., Chem. Commun., 1991, 179).

(3) The p-diketone or p-ketoester is converted to a corresponding trimethylsilylenol ether and then reacted with fluorine at −78° C. (J. Org. Chem., 52, 4309 (1987).

(4) The β-ketoester is chlorinated and then reacted with potassium fluoride in a crown ether for a long time (J. Am. Chem. Soc., 58, 1803 (1936) and Synthesis, 1977, 189).

(5) From a perfluoroolefin, for example, hexafluoropropene as a starting material, the fluorine containing β-diketone or β-ketoester is prepared through many steps (Chem. Lett., 1107 (1980) or Izv. Akad. Nauk, SSSR, Ser. Khim., 1980, 2827 (CA95-6431z)).

In addition, J. Org. Chem., 57, 2196 (1992) describes that the fluorine-containing β-ketoester is prepared by the fluorination (10 % $F_2/N_2$) of the β-ketoester (Process (6)).

But, the processes (1) and (2) have drawbacks that an expensive fluorination reagent should be used, the synthesis of the fluorination reagent is complicated, some reagents should be prepared under a very low reaction temperature condition, and they should be used immediately after their synthesis at the low temperature, since they are decomposed at room temperature.

The processes (3), (4) and (5) require multi-step reactions. Further, the process (3) has drawbacks that the fluorination should be carried out at a very low temperature, and a yield is low, the process (4) has drawbacks that an expensive crown ether should be used, a reaction time is long, and a yield is low, and the process (5) has drawbacks that the starting materials are expensive, and it is not a general process because of the small number of the available starting materials.

The above described fluorination process (6) of the β-ketoester wastes a large amount of the starting material because of an insufficient yield, and produces a variety of by-products. Since a fluorine atom has a small atomic weight (F=19) and a small polarity, in general, it is difficult to separate fluorine-containing compounds. Therefore, a preparation process which produces a variety of by-products is not an industrially advantageous process, since a complicated separation process is required after the reaction.

Accordingly, none of the above processes (1) through (6) is satisfactory, when they are carried out industrially.

SUMMARY OF THE INVENTION

An object of the present invention is to provide a process for preparing a fluorine-containing dicarbonyl compound of the formula (II), which can solve the above described drawbacks.

Another object of the present invention is to provide an industrially advantageous process which can prepare a fluorine-containing dicarbonyl compound of the formula (II) in a good yield.

DETAILED DESCRIPTION OF THE INVENTION

The present invention provides a process for preparing a fluorine-containing dicarbonyl compound of the formula:

$$R^1COCFR^2COR^3 \tag{II}$$

wherein $R^1$ is a hydrogen atom, or a substituted or unsubstituted alkyl or aryl group; $R^2$ is a hydrogen atom, a halogen atom, or a substituted or unsubstituted alkyl or aryl group; and $R^3$ is a hydrogen atom, or a substituted or unsubstituted alkyl, aryl, alkoxy or aryloxy group, provided that at least two of $R^1$, $R^2$ and $R^3$ may together form a part of a cyclic structure with or without a hetero atom, comprising reacting a dicarbonyl compound of the formula:

$$R^1COCHR^2COR^3 \tag{I}$$

wherein $R^1$, $R^2$ and $R^3$ are the same as defined above with fluorine ($F_2$) in at least one solvent selected from the group consisting of halogenated hydrocarbons having 1 to 5 carbon atoms and nitrile compounds.

Further, the present invention provides a process for preparing a fluorine-containing dicarbonyl compound of the formula (II) comprising reacting a dicarbonyl compound of the formula (I) with fluorine in a solvent in the presence of a salt, or an acid having pKa of 6 or less.

In the present invention, the alkyl group means an alkyl group having 1 to 20 carbon atom, preferably 1 to 10 carbon atoms. Optionally, the alkyl group may be substituted with a substituent such as a halogen atom, a hydroxyl group, a cyano group, an aryl group, an acyl group, an alkoxy group, an aryloxy group, an acyloxy group, an alkoxycarbonyl group, an aryloxycarbonyl group, an alkanesulfonyl group, an arylsulfonyl group, an acylamino group, and the like.

The aryl group means an aromatic group having 6 to 14 carbon atoms, preferably 6 to 10 carbon atoms. The aryl group may be substituted with a substituent such as an alkyl group, a halogen atom, a cyano group, a nitro group, an acyl group, an acyloxy group, an alkoxycarbonyl group, an aryloxycarbonyl group, an alkanesulfonyl group, an arylsulfonyl group, and the like.

The alkoxy group means an alkoxy group having 1 to 20 carbon atoms, preferably 1 to 10 carbon atoms. The alkoxy group may be substituted by the same substituent as those exemplified in connection with the alkyl group.

The aryloxy group means an arylkoxy group having 6 to 14 carbon atoms, preferably 6 to 10 carbon atoms. The aryloxy group may be substituted by the same substituent as those exemplified in connection with the aryl group.

Examples of the cyclic structure formed by the combination of $R^1$ $R^2$ and $R^3$ are a monocyclic group, a dicyclic group or a polycyclic group, having 3 to 20 members.

The halogen atom may be a fluorine atom, a chlorine atom, a bromine atom or an iodine atom.

The dicarbonyl compound of the formula (I) which is used as the raw material in the process of the present invention may be commercially available or synthesized easily by a conventional synthesis method. Examples of the dicarbonyl compound of the formula (I) are as follows:

$HCOCH_2COH$, $CH_3COCH_2COH$, $CH_3COCH_2COCH_3$,
$CH_3COCH_2COC_2H_5$, $CH_3COCH_2COC_5H_{11}$,
$CH_3COCH_2COC_8H_{17}$, $CH_3COCH_2COC_{10}H_{21}$,
$CH_3COCH(CH_3)COCH_3$, $CH_3COCH(C_8H_{17})COCH_3$,
$CH_3COCHFCOCH_3$, $CH_3COCHClCOCH_3$,
$CH_3COCHBrCOCH_3$, $CH_3COCHICOCH_3$,
$PhCOCH_2COCH_3$, $CH_3COCHPhCOCH_3$, $PhCOCH_2COPh$,
$PhCOCHFCOPh$, $CH_3COCH_2COCH_2Ph$,
$CH_3COCH(CH_2Ph)COCH_3$, $ClCH_2COCH_2COCH_3$,
$BrCH_2COCH_2COCH_3$, $CF_3COCH_2COCH_3$,
$CF_3COCH_2COCF_3$, $CF_3COCHFCOCF_3$, $C_6H_5COCH_2COC_6H_5$,
$C_6F_5COCH_2COC_6F_5$, $C_6F_5COCHFCOC_6F_5$,

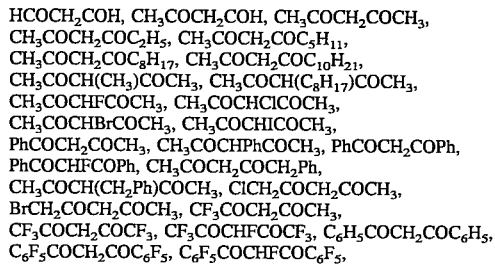

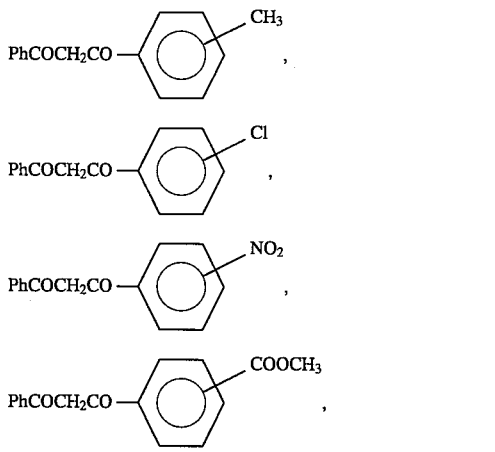

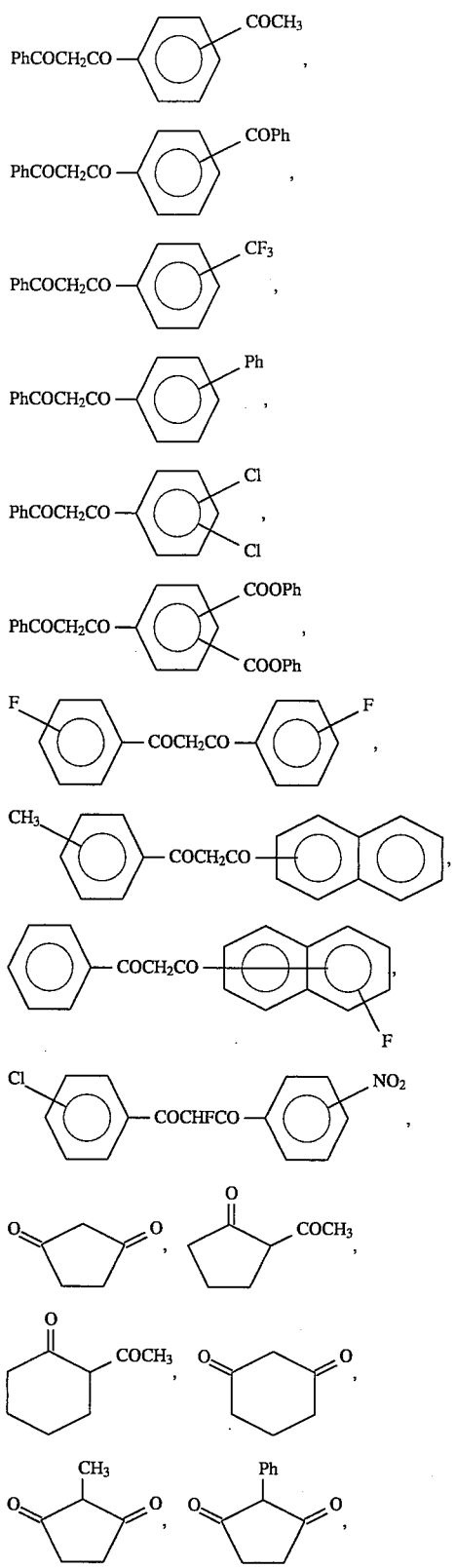

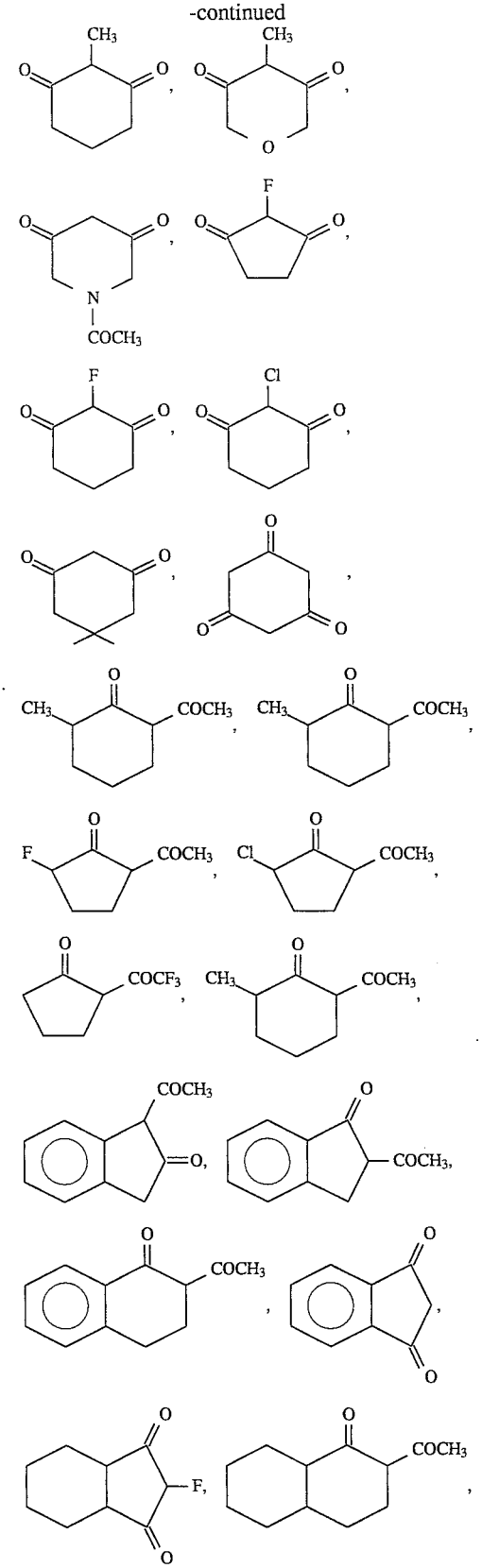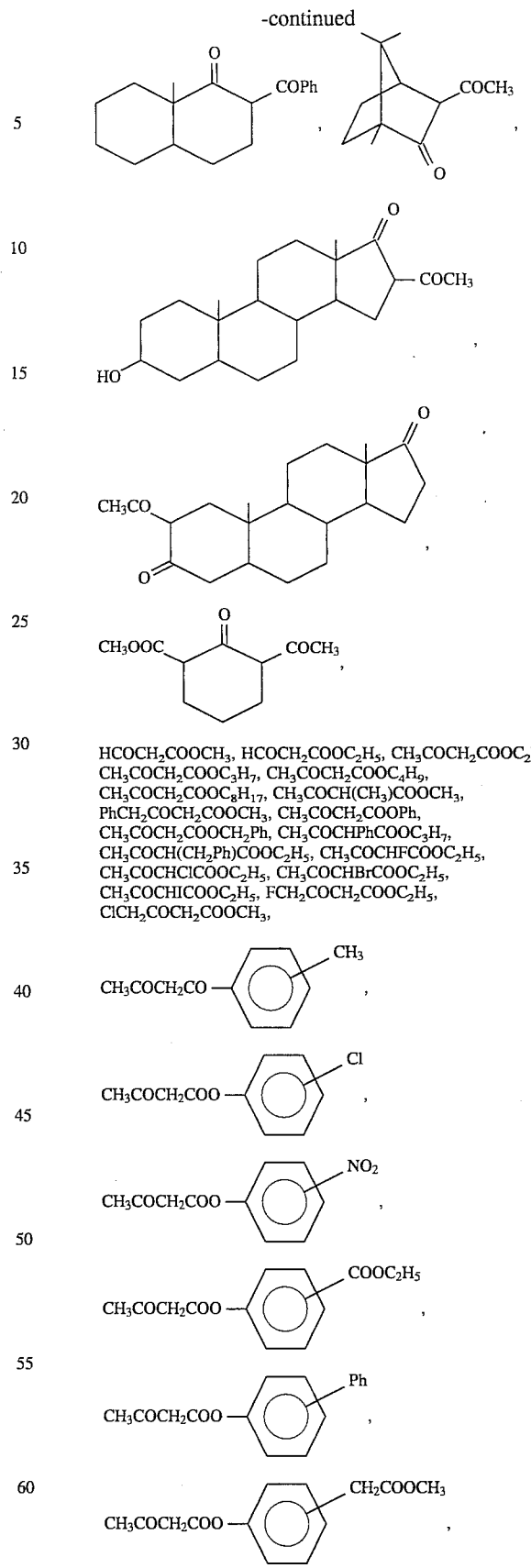

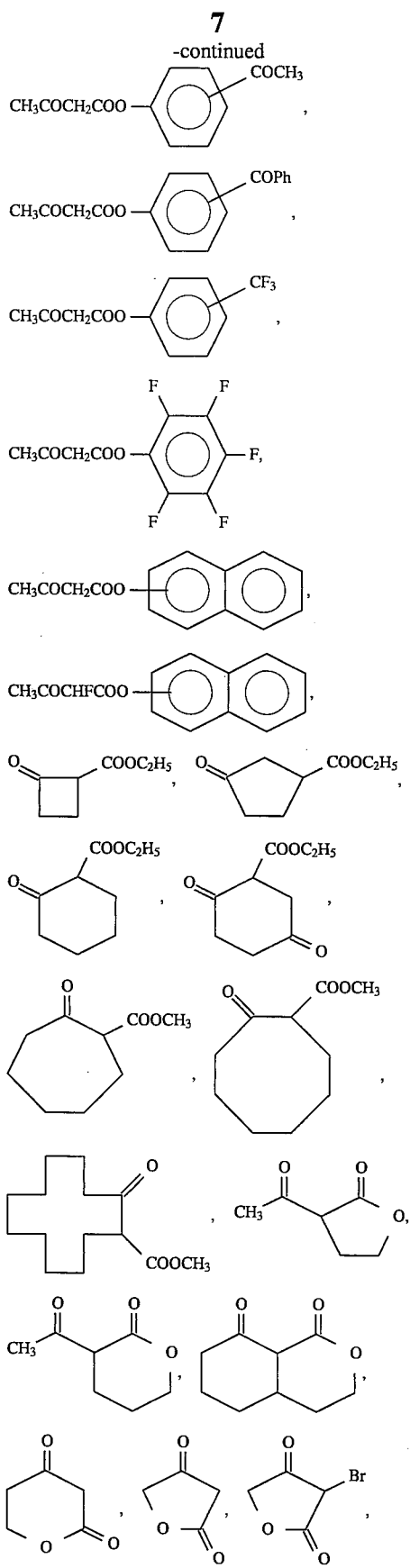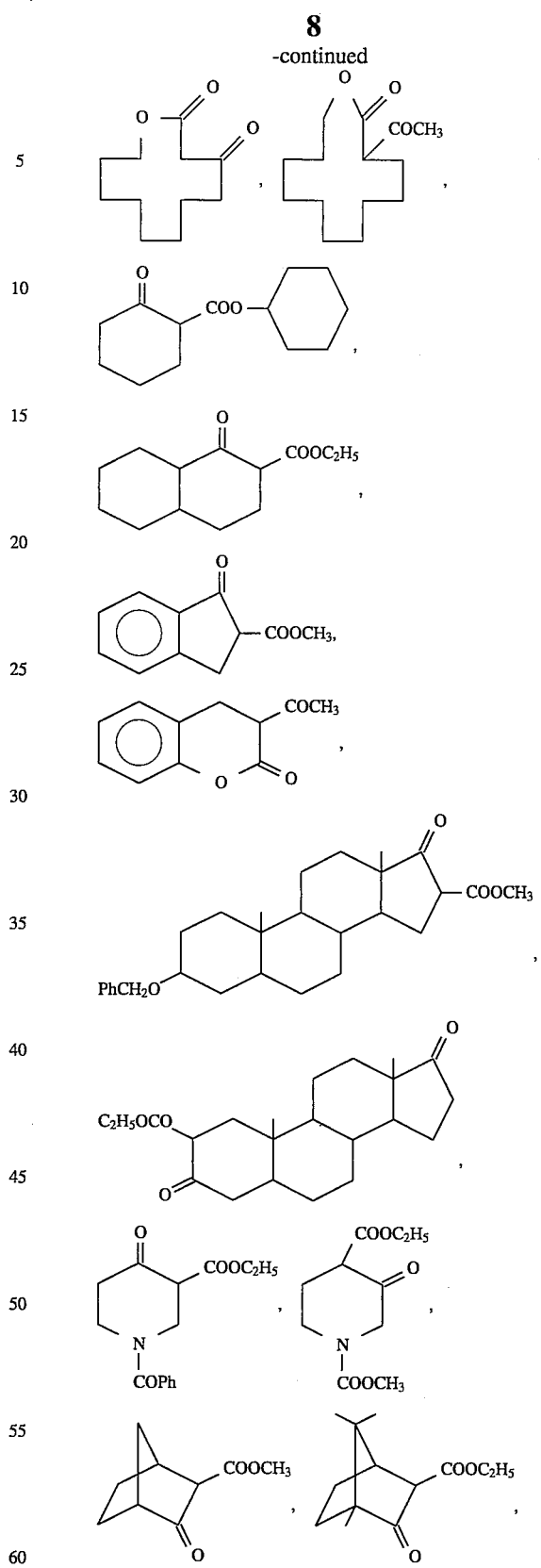
The first process of the present invention is effective, in particular, when the starting compound is a six-member compound of the formula:

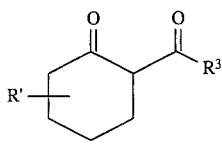

(I-1)

wherein R' is a hydrogen atom, a halogen atom, a hydroxyl group, a cyano group, or a substituted or unsubstituted alkyl, aryl, alkoxyl or aryloxy group, and $R^3$ is the same as defined above, or a dicarbonyl compound of the formula

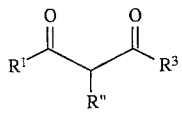

(I-2)

wherein $R^1$ and $R^2$ are the same as defined above, and R" is a hydrogen atom, a halogen atom, or a substituted or unsubstituted alkyl group.

A solvent which can be used in the first process of the present invention is a halogenated hydrocarbon having 1 to 5 carbon atoms or a nitrile compound.

Examples of the halogenated hydrocarbon are chloroform, dichloromethane, chloromethane, carbon tetrachloride, chloroethane, dichloroethane, trichloroethane, tetrachloroethane, trichlorotrifluoroethane, tetrafluoroethane, chlorotrifluoroethane, perfluoropentane, and so on. Among them, chloroform is preferred.

Examples of the nitrile compound are acetonitrile, propionitrile, and so on. Among them, acetonitrile is preferred.

The above solvent may be used in combination with other solvent so long as the characteristics of the present invention are not impaired.

The second process of the present invention is characterized in that the dicarbonyl compound of the formula (II) is reacted with fluorine in the presence of a salt, or an acid having a pKa of 6 or less.

The salt herein used means a compound prepared by a reaction of an acid and a base.

As an acid herein used, any acid to be used in conventional reactions may be used. Specific examples of the acid are:

sulfuric acid, nitric acid, phosphoric acid, polyphosphoric acid, hydrogen halides, hydrohalogenic acids, hypohalogenic acids, halogenous acids, halogenic acids, or perhalogenic acids (e.g. hydrogen fluoride, hydrofluoric acid, hydrogen chloride, hydrochloric acid, hydrogen bromide, hydrogen iodide, hypochlorous acid, chlorous acid, chloric acid, perchloric acid, perbromic acid, periodic acid, etc.);

sulfonic acids (e.g. fluorosulfonic acid, chlorosulfonic acid, methanesulfonic acid, ethanesulfonic acid, butanesulfonic acid, octanesulfonic acid, trifluoromethanesulfonic acid, difluoromethanesulfonic acid, trichloromethanesulfonic acid, perfluorobutanesulfonic acid, perfluorooctanesulfonic acid, benzenesulfonic acid, toluenesulfonic acid, nitrobenzenesulfonic acid, etc.), and polymeric sulfonic acids (e.g. polystyrenesulfonic acid, etc.);

carboxylic acids (e.g. formic acid, acetic acid, propionic acid, butyric acid, isobutyric acid, valeric acid, trimethylacetic acid, caproic acid, heptanoic acid, caprylic acid, nonaic acid, chloroacetic acid, bromoacetic acid, dichloroacetic acid, trichloroacetic acid, trifluoroacetic acid, glycolic acid, lactic acid, benzoic acid, oxalic acid, succinic acid, etc.), and polymeric carboxylic acids (e.g. polyacrylic acid, etc.);

Lewis acids (e.g. $BF_3$, $BCl_3$, $B(OCH_2)_3$, $B(OCOCH_3)_3$, $AlCl_3$, $SbF_3$, $SbCl_3$, $SbF_6$, $PF_3$, $PF_5$, $AsP_3$, $AsCl_3$, $AsF_5$, $TiCl_4$, etc.) and their complexes with ethers and the like; acids comprising a Lewis acid and a hydrogen halide (e.g. $HBF_5$, $HSbF_3$, $HPF_5$, $HAsF_6$, $HSbCl_3$, etc.) and their complexes with ehter and the like; or carbonic acid.

As the base constituting the salt, any base to be used in conventional reactions may be used. Specific examples of the base are:

metal hydroxides (e.g. sodium hydroxide, potassium hydroxide, lithium hydroxide, rubidium hydroxide, cesium hydroxide, magnesium hydroxide, calcium hydroxide, barium hydroxide, etc.);

metal alkoxides (e.g. sodium methoxide, sodium ethoxide, sodium butoxide, potassium methoxide, potassium ethoxide, potassium butoxide, lithium methoxide, lithium ethoxide, etc.);

metal hydrides (e.g. sodium hydride, potassium hydride, lithium hydride, calcium hydride, etc.);

alkali metals (e.g. sodium, potassium, lithium, etc.);

metal oxides (e.g. magnesium oxide, calcium oxide, etc.);

ammonia and amines (e.g. methylamine, ethylamine, diethylamine, triethylamine, trimethylamine, propylamine, butylamine, tributylamine, aniline, dimethylaniline, pyridine, methylpyridine, dimethylpyridine, trimethylpyridine, halopyridine, ethylenediamine, N,N,N',N'-tetramethylenediamine, 1,5-diazabicyclo[4.3.0]-nonan-5-ene, 1,4-diazabicyclo[2.2.2]octane, quinoline, etc.);

polymeric amines (e.g. polyallylamine, polyvinylpyridine, etc.);

ammonium hydroxide, salts of ammonium hydroxide (e.g. tetramethylammonium hydroxide, tetraethylammonium hydroxide, tetrabutylammonium hydroxide, octyltriethylammonium hydroxide, benzyltrimethylammonium hydroxide, etc.), or polymeric ammonium hydroxide salts (e.g. Amberlite resin, etc.).

The salt to be used in the present invention is a compound synthesized by a reaction of the above acid and the above base. Specific examples of the salt are:

metal or amine salts of sulfuric acid or sulfonic acids (e.g. sodium sulfate, sodium hydrogensulfate, potassium sulfate, potassium hydrogensulfate, lithium sulfate, cesium sulfate, calcium sulfate, magnesium sulfate, ammonium sulfate, triethylammonium sulfate, pyridinium sulfate, trimethylpyridinium sulfate, polyallylammonium sulfate, polyvinylpyridinium sulfate, sodium methanesulfonate, ammonium methanesulfonate, tetramethylammonium methanesulfonate, potassium ethanesulfonate, lithium butanesulfohate, sodium benzenesulfonate, sodium toluenesulfonate, sodium trifluoromethanesulfonate, sodium polystyrenesulfonate,, etc.);

metal or amine salts of carboxylic acids (e.g. sodium formate, ammonium formate, sodium acetate, potassium acetate, lithium acetate, magnesium acetate, calcium acetate, ammonium acetate, methylammonium acetate, diethylammonium acetate, triethylammonium acetate, tetraethylammonium acetate, pyridinium acetate, sodium propionate, potassium propionate, sodium butyrate, polyallylammonium acetate, polyvinylpyridinium acetate, sodium isobutyrate, sodium valerate, sodium nonanate, sodium chloroacetate, sodium bromoacetate, sodium trichloroacetate, sodium trifluoroacetate, sodium glycolate, sodium lactate, sodium benzoate, sodium oxalate, sodium succinate, polysodium acrylate, etc.);

metal or amine salts of hydrogen halides, hydrohalogenic acids, hypohalogenic acids, halogenous acids, halogenic acids, or perhalogenic acids (e.g. sodium fluoride, potassium fluoride, cesium fluoride, ammonium fluoride, tetraethylammonium fluoride, tetrabutylammonium fluoride, polyallylammonium fluoride, sodium chloride, ammonium chloride, sodium hypochlorite, sodium chlorite, sodium chlorate, sodium perchlorate, sodium perbromate, sodium periodate, etc.);

metal or amine salts of phosphoric acid (e.g. sodium phosphate, potassium phosphate, sodium hydrogenphosphate, sodium dihydrogenphosphate, ammonium phosphate, pyridinium phosphate, etc.);

metal or amine salts of nitric acid (e.g. sodium nitrate, potassium nitrate, ammonium nitrate, pyridinium nitrate, etc.);

metal or amine salts of carbonic acid (e.g. sodium carbonate, lithium carbonate, potassium carbonate, sodium hydrogencarbonate, ammonium carbonate, etc.);

metal or amine salts of acids comprising a Lewis acid and a hydrogen halide (e.g. $NaBF_4$, $KBF_4$, $LIBF_4$, $NaSbF_6$, $NaAsF_6$, $NaPF_5$, $NH_4BF_4$, $NH_4SbF_6$, $NH_4PF_6$, etc.);

phosphonium salts (e.g. tetramethylphosphonium fluoride, tetrametylphosphonium acetate, tetraphenylphosphonium fluoride, etc.);

and mixtures thereof.

An amount of the salt used in the second process of the present invention is selected from a range from a catalytic amount to a large excess amount. Preferably, an amount of the salt is from 0.1 to 20 moles, more preferably from 0.5 to 10 moles per one mole of the dicarbonyl compound of the formula (II).

The acid to be used in the second process of the present invention is an acid having pKa of 6 or less, preferably a stronger acid than acetic acid (pKa 4.56). Examples of such acid are:

sulfuric acid, nitric acid, phosphoric acid, polyphosphoric acid, hydrogen halides, hydrohalogenic acids, hypohalogenic acids, halogenous acids, halogenic acids, or perhalogenic acids such as hydrogen fluoride, hydrofluoric acid, hydrogen chloride, hydrochloric acid, hydrogen bromide, hydrogen iodide, hypochlorous acid, chlorous acid, chloric acid, perchloric acid, perbromic acid, periodic acid, etc.);

sulfonic acids (e.g. fluorosulfonic acid, chlorosulfonic acid, methanesulfonic acid, ethanesulfonic acid, butanesulfonic acid, octanesulfonic acid, trifluoromethanesulfonic acid, difluoromethanesulfonic acid, trichloromethanesulfonic acid, perfluorobutaneo sulfonic acid, perfluorooctanesulfonic acid, benzenesulfonic acid, toluenesulfonic acid, nitrobenzenesulfonic acid, etc.), and polymeric sulfonic acids (e.g. polystyrenesulfonic acid, etc.);

carboxylic acids (e.g. formic acid, chloroacetic acid, bromoacetic acid, dichloroacetic acid, trichloroacetic acid, trifluoroacetic acid, glycolic acid, lactic acid, benzoic acid, oxalic acid, succinic acid, etc.);

Lewis acids (e.g. $BF_3$, $BCl_3$, $B(OCH_2)_3$, $B(OCOCH_3)_3$, $AlCl_3$, $SbF_3$, $SbCl_3$, $SbF_6$, $PF_3$, $PF_5$, $AsP_3$, $AsCl_3$, $AsF_5$, $TiCl_4$, etc.) and their complexes with ethers and the like; acids comprising a Lewis acid and a hydrogen halide (e.g. $HBF_5$, $HSbF_3$, $HPF_5$, $HAsF_6$, $HSbCl_3$, etc.) and their complexes with ehter and the like; and their mixtures.

When a weak acid such as acetic acid is used as a solvent, an acid different from the weak acid is used.

An amount of the acid used in the present invention is from a catalytic amount to a large excess amount based on the amount of the dicarbonyl compound of the formula (II). This acid may be used as the solvent.

Different from the first process, a kind of the solvent is not limited in the second process of the present invention. In addition to the halogenated hydrocarbons and the nitrile compounds used in the first process, there can be used other halogenated hydrocarbons (e.g. perfluorohexane, perfluorooctane, etc.), water, the above described acids, acetic acid, propionic acid, butyric acid, isobutyric acid, alcohols (e.g. methanol, ethanol, trifluoroethanol, propanol, isopropanol, hexafluoroisopropanol, butanol, sec.-butanol, tert.-butanol, etc.), carboxylic anhydrides (e.g. acetic anhydride, propionic anhydride, formic anhydride, etc.), ethers (e.g. diethyl ether, dipropyl ether, dibutyl ether, tetraydrofuran, etc.), ketones (e.g. acetone, methyl ethyl ketone, diethyl ketone, etc.), alkanes (e.g. hexane, octane, cyclohexane, etc.), esters (e.g. ethyl acetate, ethyl formate, propyl formate, methyl propionate, ethyl propionate, etc.), and their mixtures.

Among them, the aliphatic acids, halogenated hydrocarbons, alcohols, nitrile compounds and their mixtures are preferred, and the aliphatic acids and nitrile compounds, in particular, their mixture are more preferred. Examples of the aliphatic acid to be used as the solvent are formic acid, acetic acid, propionic acid, butyric acid, isobutyric acid, and trifluoroacetic acid. Among them, acetic acid is preferred.

Preferred examples of the nitrile compound are acetonitrile and propionitrile. Among them, acetonitrile is more preferred.

Fluorine ($F_2$) to be used in the present invention is preferably used in a diluted form with an inert gas so that a volume percentage of the inert gas is from 99.9% to 50%, to suppress the violent reactivity of the fluorine. Examples of the diluent inert gas are nitrogen, helium argon, carbon dioxide, and so on.

An amount of the fluorine may not be uniformly determined, since it varies with an introduction manner, a reaction temperature, a kind of the reaction solvent, a reaction apparatus, and so on. A person skilled in the art can easily determine the amount of the fluorine to be used by carrying out some simple preliminary experiments with aiming an amount necessary for substantially disappearing the dicarbonyl compound of the formula (I) which is the starting material.

A reaction temperature is selected from a range between −120° C. and +80° C. To carry out the reaction effectively in a high yield, the reaction temperature is preferably from −100° C. to +50° C., in particular, from −80° C. to +30° C.

When the aliphatic acid is used as the solvent, and the base such as the metal, metal hydroxide, metal hydride, metal alkoxide, metal oxide or amine is used, apparently, a metal salt or amine salt of the aliphatic acid is formed through the reaction between the solvent and the base. Similarly, when the above acidic solvent such as hydrogen fluoride or phosphoric acid is used, the solvent reacts with the base to form a corresponding salt.

In the case of the dicarbonyl compound of the formula (I) in which $R^2$ is a hydrogen, a product which is produced after twice repeating the reaction of the present invention according to the following reaction formula, that is, a fluorine-containing carbonyl compound of the formula (II) in which $R^2$ is a fluorine atom is obtained:

$R^1COCH_2COR^3 \xrightarrow{F_2} R^1COCHFCOR^3 \xrightarrow{F_2} R^1COCF_2COR^3$ Alternatively, when $R^2$ in the formula (I) is a fluorine atom, the difluorinated dicarbonyl compound can be obtained by a single step.

According to the present invention, the fluorine-containing carbonyl compound of the formula (II) is prepared in a good yield in a single step from the dicarbonyl compound of the formula (I), which is commercially available or easily synthesized, as the starting material using cheap fluorine gas. This fluorine-containing dicarbonyl compound can be used as a highly active intermediate of agrochemicals, and the like.

EXAMPLES

The present invention will be illustrated by Examples, which do not limit the scope of the invention in any way.

Example 1

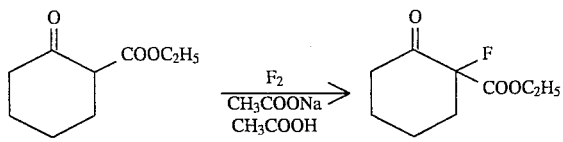

A mixed gas of 5% $F_2$/95% $N_2$ was flowed at a rate of 15 ml/min. in a mixture of ethyl cyclohexanone-2-carboxylate (340 mg, 2 mmol), sodium acetate (165 mg, 2 mmol) and acetic acid (2 ml), while stirring and cooling on a water bath at 12° C. An amount of supplied $F_2$ was 86 ml (3.8 mmol).

After the reaction, the reaction mixture was quantitatively analyzed by $^{19}$F-NMR to find that ethyl 2-fluorocyclohexnanone-2-carboxylate was formed in a yield of 88%. The structure of the product was confirmed by comparing the product, which was isolated by post treatment, with the structure of the standard sample according to the conventional method.

Examples 2–22

Under the conditions shown in Table 1, ethyl cyclohexanone-2-carboxylate was fluorinated in the same manner as in Example 1. The results are shown in Table 1 together with those of Example 1.

TABLE 1

| Ex. No. | Amount of dicarbonyl compound (mmol) | $F_2$ concentration | $F_2$ amount (mmol) | Solvent and amount | Additive and amount | Reaction temp (°C.) | Yield of F-cont. dicarbonyl compound (%) |
|---|---|---|---|---|---|---|---|
| 1 | 2 | 5% $F_2$/95% $N_2$ | 3.8 | $CH_3COOH$ (2 ml) | $CH_3COONa$ (2 mmol) | 12 | 88 |
| 2 | 2 | ↑ | 3.8 | $CHCl_3$ (4 ml) | None | 0 | 86 |
| 3 | 2 | ↑ | 4 | $CHCl_3$ (4 ml) | None | −10 | 80 |
| 4 | 2 | ↑ | 6.8 | $CHCl_3$ (4 ml) | NaF (4 mmol) | 0 | 75 |
| 5 | 2 | ↑ | 3.5 | $CHCl_3$ (4 ml) | $H_2SO_4$ (0.16 mmol) | 0 | 85 |
| 6 | 2 | ↑ | 3.5 | $CHCl_3$ (4 ml) | $H_2SO_4$ (1 mol) | 0 | 87 |
| 7 | 2 | ↑ | 4 | $CH_3COOH$ (4 ml) | $H_2SO_4$ (1 mol) | 10 | 95 |
| 8 | 2 | ↑ | 4 | $CH_3COOH$ (4 ml) | $H_3PO_4$ (2 mo l) | 12 | 83 |
| 9 | 2 | ↑ | 3.6 | $CH_3COOH$ (10 ml) | $CH_3COONa$ (10 mol) | 12 | 84 |
| 10 | 5.9 | ↑ | 11.8 | $CH_3COOH/H_2O(6/1)$ (3.5 ml) | $CH_3COONa$ (5.9 mol) | 12 | 76 |
| 11 | 2 | ↑ | 5.1 | $CH_3COOH$ (10 ml) | $CH_3COOK$ (10 mol) | 12 | 76 |
| 12 | 2 | ↑ | 4 | $CH_3COOH$ (10 ml) | $CH_3COONH_4$ (10 mmol) | 12 | 70 |
| 13 | 2 | ↑ | 4 | $CH_3COOH$ (4 ml) | $CH_3COOLi$ (10 mmol) | 12 | 81 |
| 14 | 2 | ↑ | 4 | $CH_3COOH$ (10 ml) | $CCl_3COONa$ (10 mmol) | 12 | 82 |
| 15 | 2 | 5% $F_2$/95% $N_2$ | 4 | $CH_3CN/CH_3OH$ (1/1) (4 ml) | $CH_3COONa$ | 0 | 79 |
| 16 | 118 | 10% $F_2$/90% $N_2$ | 135 | $CH_3CN/CH_3COOH$ (1/1) (120 ml) | $CH_3COONa$ (153 mmol) | 5 | 79 |
| 17 | 118 | ↑ | 135 | $CH_3CN/CH_3COOH$ (2/1) (120 ml) | $CH_3COONa$ (153 mmol) | 5 | 83 |

TABLE 1-continued

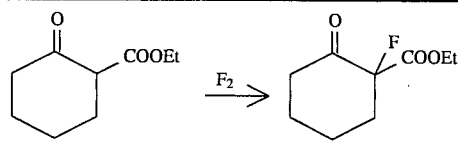

| Ex. No. | Amount of dicarbonyl compound (mmol) | $F_2$ concentration | $F_2$ amount (mmol) | Solvent and amount | Additive and amount | Reaction temp (°C.) | Yield of F-cont. dicarbonyl compound (%) |
|---|---|---|---|---|---|---|---|
| 18 | 118 | ↑ | 146 | $CH_3CN$/$CH_3COOH$ (5/1) (120 ml) | $CH_3COONa$ (153 mmol) | 5 | 90 |
| 19 | 118 | ↑ | 156 | $CH_3CN$/$CH_3COOH$ (10/1) (110 ml) | $CH_3COONa$ (153 mmol) | 5 | 89 |
| 20 | 118 | ↑ | 152 | $CH_3CN$/$CH_3COOH$ (20/1) (105 ml) | $CH_3COONa$ (153 mmol) | 5 | 75 |
| 21 | 118 | ↑ | 155 | $CH_3CN$/$CH_3COOH$ (5/1) (120 ml) | $CH_3COONa$ (155 mmol) | −10 | 76 |
| 22 | 118 | ↑ | 152 | $CH_3CN$/$CH_3COOH$ (1/1) (120 ml) | NaOH (177 mmol) | 0 | 80 |

Examples 23 to 31

Under the conditions shown in Table 2, various dicarbonyl compounds were fluorinated in the same manner as in Example 1. The results are shown in Table 2. The structures of the products were identified by comparing the spectra of the products with those of the standard samples.

Comparative Examples 1 to 8

Under the conditions shown in Table 3, various dicarbonyl compounds were fluorinated in the same manner as in Example 1. The results are shown in Table 3. The structures of the products were identified by comparing the spectra of the products with those of the standard samples.

TABLE 2

| Ex. No. | Dicarbonyl compound | Amount of dicarbonyl compound | F₂ concentration | F₂ amount (mmol) | Solvent (amount) | Additive (mmol) | Reaction temp. | Product | Yield (%) |
|---|---|---|---|---|---|---|---|---|---|
| 23 | ethyl acetoacetate | 2 mmol | 5% F₂/95% N₂ | 6.4 | CHCl₃ (4 ml) | None | 0° C. | ethyl 2-fluoroacetoacetate | 82 |
| 24 | 2-acetylcyclohexanone | 2 mmol | ↑ | 7.5 | CHCl₃ (4 ml) | None | 0° C. | 2-acetyl-2-fluorocyclohexanone | 96 |
| 25 | 2-acetylcyclohexanone | 2 mmol | ↑ | 3.9 | CH₃CN (4 ml) | None | 0° C. | 2-acetyl-2-fluorocyclohexanone | 79 |
| 26 | dibenzoylmethane | 2 mmol | ↑ | 6.4 | CHCl₃ (4 ml) | None | 0° C. | 2-fluoro-1,3-diphenyl-1,3-propanedione | 75 |
| 27 | ethyl acetoacetate | 2 mmol | 5% F₂/95% N₂ | 3.8 | CHCl₃ (4 ml) | H₂SO₄ 1 mmol | 0° C. | ethyl 2-fluoroacetoacetate | 71 |
| 28 | 2-acetylcyclohexanone | 2 mmol | ↑ | 4 | CH₃COOH (4 ml) | CH₃COONa 2 mmol | 12° C. | 2-acetyl-2-fluorocyclohexanone | 92 |

Note: Ex. 26 also shows a difluorinated byproduct (2,2-difluoro-1,3-diphenyl-1,3-propanedione) at 21% yield.

TABLE 2-continued

| Ex. No. | Dicarbonyl compound | Amount of dicarbonyl compound | F$_2$ concentration | F$_2$ amount (mmol) | Solvent (amount) | Additive (mmol) | Reaction temp. | Product | Yield (%) |
|---|---|---|---|---|---|---|---|---|---|
| 29 | (2-COOEt cyclopentanone) | 2 mmol | ↑ | 3.6 | CH$_3$CN/CH$_3$COOH (10/1) (4 ml) | CH$_3$COONa 5 mmol | 0° C. | (2-F, 2-COOEt cyclopentanone) | 81 |
| 30 | (2-methyl-1,3-cyclopentanedione) | 2 mmol | ↑ | 4 | CH$_3$COOH (4 ml) | CH$_3$COONa | 12° C. | (2-F, 2-methyl-1,3-cyclopentanedione) | 73 |
| 31 | (PhCOCH$_2$COPh) | 2 mmol | ↑ | 4.9 | CH$_3$COOH (4 ml) | CH$_3$COONa 2 mmol | 12° C. | (PhCOCHFCOPh and PhCOCF$_2$COPh) | 27, 66 |

TABLE 3

| Ex. No. | Dicarbonyl compound | Amount of dicarbonyl compound | F₂ concentration | F₂ amount (mmol) | Solvent (amount) | Additive (mmol) | Reaction temp. | Product | Yield (%) |
|---|---|---|---|---|---|---|---|---|---|
| 1 | CH₃-CO-CH₂-COOEt | 2 mmol | 5% F₂/95% N₂ | 4.8 | None | None | 0° C. | CH₃-CO-CF₂-COOEt | 43 |
| 2 | 2-carboethoxycyclohexanone | 2 mmol | ↑ | 4 | None | None | 0° C. | 2-fluoro-2-carboethoxycyclohexanone | 69 |
| 3 | 2-carboethoxycyclopentanone | 2 mmol | ↑ | 4 | CH₃COOH (4 ml) | None | 16° C. | 2-fluoro-2-carboethoxycyclohexanone | 46 |
| 4 | 2-carboethoxycyclopentanone | 2 mmol | ↑ | 4 | CH₃COOH (10 ml) | None | ↑ | 2-fluoro-2-carboethoxycyclohexanone | 22 |
| 5 | 2-carboethoxycyclohexanone | 2 mmol | ↑ | 4 | H₂O (4 ml) | NaOH 2 mmol | 0° C. | 2-fluoro-2-carboethoxycyclohexanone | 16 |
| 6 | 2-carboethoxycyclohexanone | 1 mmol | 5% F₂/95% N₂ | 1.4 | THF (2 ml) | NaH 1 mmol | −53° C. | 2-fluoro-2-carbooethoxycyclopentanone | 12 |

What is claimed is:

1. A process for preparing a fluorine-containing dicarbonyl compound of the formula:

$$R^1COCFR^2COR^3 \quad (II)$$

wherein $R^1$ is a hydrogen atom, or a substituted or unsubstituted alkyl or aryl group; $R^2$ is a hydrogen atom, a halogen atom, or a substituted or unsubstituted alkyl or aryl group; and $R^3$ is a hydrogen atom, or a substituted or unsubstituted alkyl, aryl, alkoxy or aryloxy group, provided that at least two of $R^1$, $R^2$ and $R^3$ may together form a part of a cyclic structure with or without a hetero atom, comprising reacting a dicarbonyl compound of the formula:

$$R^1COCHR^2COR^3 \quad (I)$$

wherein $R^1$, $R^2$ and $R^3$ are the same as defined above with fluorine ($F_2$) in at least one solvent selected from the group consisting of halogenated hydrocarbons having 1 to 5 carbon atoms and nitrile compounds.

2. The process according to claim 1, wherein said dicarbonyl compound (I) is a six-membered compound of the formula:

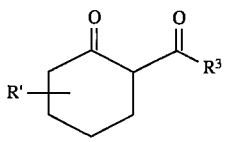
(I-1)

wherein R' is a hydrogen atom, a halogen atom, a hydroxyl group, a cyano group, or a substituted or unsubstituted alkyl, aryl, alkoxyl or aryloxy group, and $R^3$ is the same as defined above, or a dicarbonyl compound of the formula

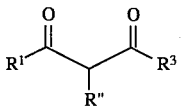
(I-2)

wherein $R^1$ and $R^2$ are the same as defined above, and R" is a hydrogen atom, a halogen atom, or a substituted or unsubstituted alkyl group.

3. The process according to claim 1, wherein said solvent is chloroform or acetonitrile.

4. A process for preparing a fluorine-containing dicarbonyl compound of the formula:

$$R^1COCFR^2COR^3 \quad (II)$$

wherein $R^1$ is a hydrogen atom, or a substituted or unsubstituted alkyl or aryl group; $R^2$ is a hydrogen atom, a halogen atom, or a substituted or unsubstituted alkyl or aryl group; and $R^3$ is a hydrogen atom, or a substituted or unsubstituted alkyl, aryl, alkoxy or aryloxy group, provided that at least two of $R^1$, $R^2$ and $R^3$ may together form a part of a cyclic structure with or without a hetero atom, comprising reacting a dicarbonyl compound of the formula:

$$R^1COCHR^2COR^3 \quad (I)$$

wherein $R^1$, $R^2$ and $R^3$ are the same as defined above with fluorine ($F_2$) in a solvent in the presence of a salt, or an acid having pKa of 6 or less.

5. The process according to claim 4, wherein said solvent is at least one solvent selected from the group consisting of nitrile compounds and aliphatic acids.

6. The process according to claim 4, wherein said solvent is a mixture of a nitrile compound and an aliphatic acid.

7. The process according to claim 4, wherein an acid having pKa of less than 4.5 is used.

8. The process according to claim 1, wherein said alkyl group is an alkyl group having 1 to 20 carbon atoms which is unsubstituted or substituted with a substituent selected from the group consisting of a halogen atom, a hydroxyl group, a cyano group, an aryl group, an acyl group, an alkoxy group, an aryloxy group, an acyloxy group, an alkoxycarbonyl group, an aryloxycarbonyl group, an alkanesulfonyl group, an arylsulfonyl group and an acylamino group;

wherein said aryl group is an aromatic group having 6 to 14 carbon atoms which is unsubstituted or substituted with a substituent selected from the group consisting of an alkyl group, a halogen atom, a cyano group, a nitro group, an acyl group, an acyloxy group, an alkoxycarbonyl group, an aryloxycarbonyl group, an alkanesulfonyl group, and an arylsulfonyl group;

wherein the alkoxy group has 1 to 20 carbon atoms and is unsubstituted or substituted with a substituent selected from the same group of substituents for the alkyl group;

wherein the aryloxy group is an arylkoxy group having 6 to 14 carbon atoms which is unsubstituted or substituted with a substituent selected from the same group of substituents for the aryl group; and wherein said cyclic structure formed by at least two of $R^1$, $R^2$ and $R^3$ is a monocyclic, dicyclic or polycyclic group having 3 to 20 members.

9. The process according to claim 8, wherein said alkyl group has 1 to 10 carbon atoms, the aryl group has 6 to 10 carbon atoms, the alkoxy group has 1 to 10 carbon atoms, and the aryloxy group has 6 to 10 carbon atoms.

10. The process according to claim 1, wherein the halogenated hydrocarbon having 1 to 5 carbon atoms is the solvent and is selected from the group consisting of chloroform, dichloromethane, chloromethane, carbon tetrachloride, chloroethane, dichloroethane, trichloroethane, tetrachloroethane, trichlorotrifluoroethane, tetrafluoroethane, chlorotrifluoroethane and perfluoropentane.

11. The process according to claim 1, wherein the solvent is a nitrile compound selected from the group consisting of acetonitrile and propionitrile.

12. The process according to claim 4, wherein said alkyl group is an alkyl group having 1 to 20 carbon atoms which is unsubstituted or substituted with a substituent selected from the group consisting of a halogen atom, a hydroxyl group, a cyano group, an aryl group, an acyl group, an alkoxy group, an aryloxy group, an acyloxy group, an alkoxycarbonyl group, an aryloxycarbonyl group, an alkanesulfonyl group, an arylsulfonyl group and an acylamino group;

wherein said aryl group is an aromatic group having 6 to 14 carbon atoms which is unsubstituted or substituted with a substituent selected from the group consisting of an alkyl group, a halogen atom, a cyano group, a nitro group, an acyl group, an acyloxy group, an alkoxycarbonyl group, an aryloxycarbonyl group, an alkanesulfonyl group, and an arylsulfonyl group;

wherein the alkoxy group has 1 to 20 carbon atoms and is unsubstituted or substituted with a substituent selected from the same group of substituents for the alkyl group;

wherein the aryloxy group is an arylkoxy group having 6 to 14 carbon atoms which is unsubstituted or substituted with a substituent selected from the same group of substituents for the aryl group; and wherein said cyclic structure formed by at least two of $R^1$, $R^2$ and $R^3$ is a monocyclic, dicyclic or polycyclic group having 3 to 20 members.

13. The process according to claim 12, wherein said alkyl group has 1 to 10 carbon atoms, the aryl group has 6 to 10 carbon atoms, the alkoxy group has 1 to 10 carbon atoms, and the aryloxy group has 6 to 10 carbon atoms.

* * * * *